United States Patent
Jacob

(10) Patent No.: US 6,514,075 B1
(45) Date of Patent: Feb. 4, 2003

(54) DENTAL CURING APPARATUS FOR LIGHT-SENSITIVE MATERIALS

(76) Inventor: Gregory S. Jacob, 9672 Reding Cir., Des Plaines, IL (US) 60016

( * ) Notice: Subject to any disclaimer, the term of this patent is extended or adjusted under 35 U.S.C. 154(b) by 0 days.

(21) Appl. No.: 09/658,322

(22) Filed: Sep. 8, 2000

Related U.S. Application Data

(60) Continuation-in-part of application No. 09/469,923, filed on Dec. 22, 1999, now abandoned, which is a division of application No. 09/153,653, filed on Sep. 15, 1998, now Pat. No. 6,077,073.

(51) Int. Cl.[7] .............................................. A61C 1/00
(52) U.S. Cl. ....................................................... 433/29
(58) Field of Search ........................... 433/29; 606/13, 606/14, 17; 600/241, 245, 249

(56) References Cited

U.S. PATENT DOCUMENTS

| | | | | |
|---|---|---|---|---|
| 936,499 A | * | 10/1909 | Werner | 600/245 |
| 1,533,605 A | * | 4/1925 | Peton et al. | 600/245 |
| 2,528,458 A | * | 10/1950 | Stone | 600/245 |
| 2,800,896 A | * | 7/1957 | Thum | 600/245 |
| 4,643,172 A | * | 2/1987 | Taff et al. | 600/245 |
| 4,757,381 A | * | 7/1988 | Cooper et al. | 433/29 |
| 5,201,655 A | | 4/1993 | Friedman | |
| 5,290,169 A | | 3/1994 | Friedman et al. | |
| 5,316,473 A | | 5/1994 | Hare | |
| 5,328,368 A | * | 7/1994 | Lansing et al. | 433/29 |
| 5,353,786 A | * | 10/1994 | Wilk | 600/245 |
| 5,415,543 A | | 5/1995 | Rozmajzl, Jr. | |
| 5,487,662 A | | 1/1996 | Kipke et al. | |
| 5,634,711 A | | 6/1997 | Kennedy et al. | |
| 5,702,250 A | | 12/1997 | Kipke | |
| 5,711,665 A | | 1/1998 | Adam et al. | |
| 5,718,577 A | | 2/1998 | Oxman et al. | |
| 5,782,896 A | * | 7/1998 | Chen et al. | 607/88 |
| 5,865,621 A | * | 2/1999 | Calderwood | 433/29 |

* cited by examiner

Primary Examiner—Todd E. Manahan
(74) Attorney, Agent, or Firm—Pauley Petersen Kinne & Erickson

(57) ABSTRACT

A dental curing apparatus for light-sensitive materials is disclosed. A light source for curing an adhesive is housed within a clear, transparent and/or translucent housing constructed of either a solid, such as a poured resin, or a hollow structure. The housing shape is selected to conform to an approximate shape of dentition. The housing is mountable within a disposable oversertion sheath. During use, the light source for curing an adhesive transmits light which cures the adhesives, sealants and/or whitening or coloring agents.

15 Claims, 14 Drawing Sheets

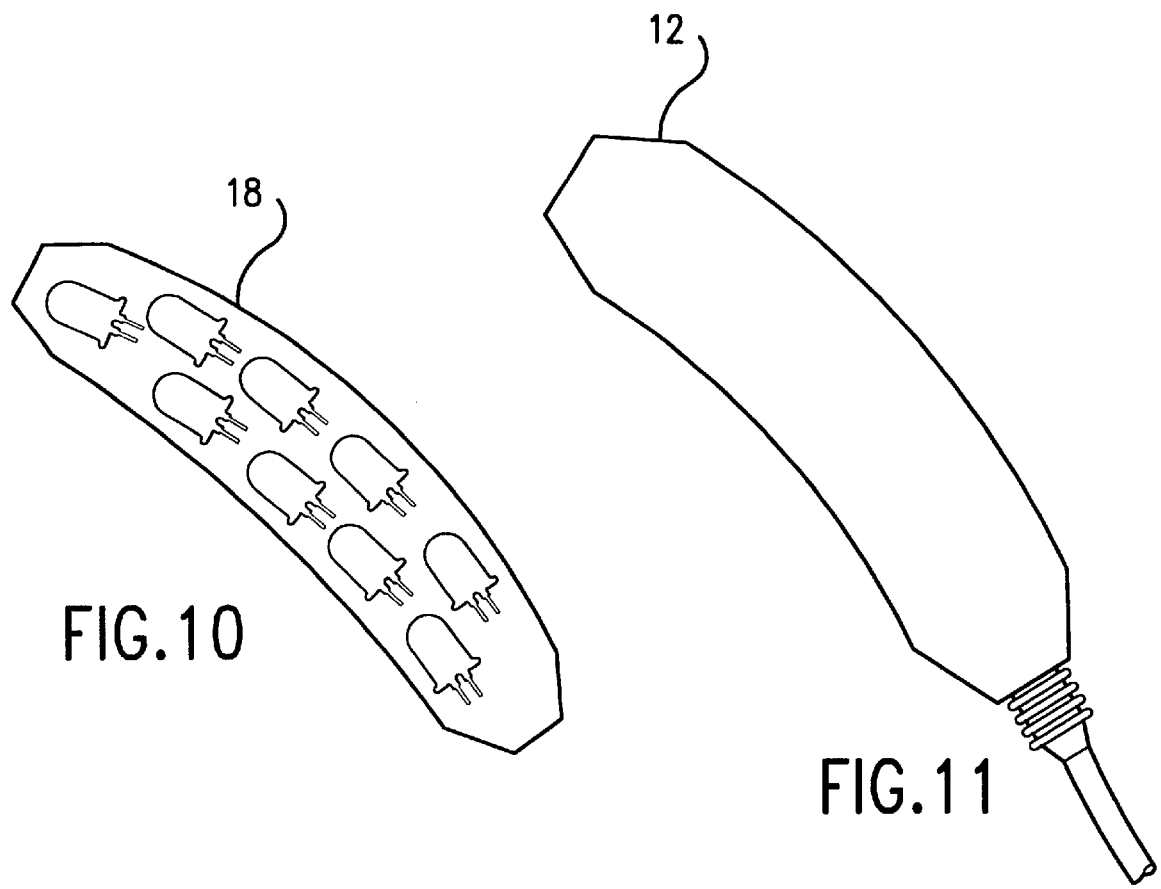
FIG.10
FIG.11
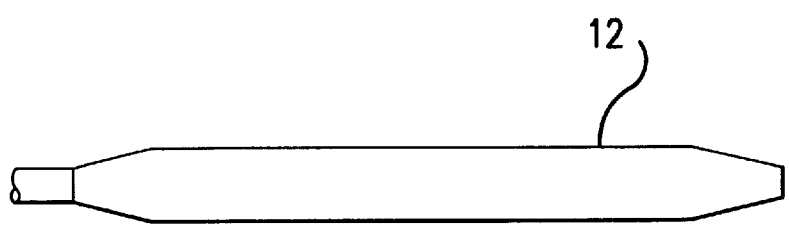
FIG.12

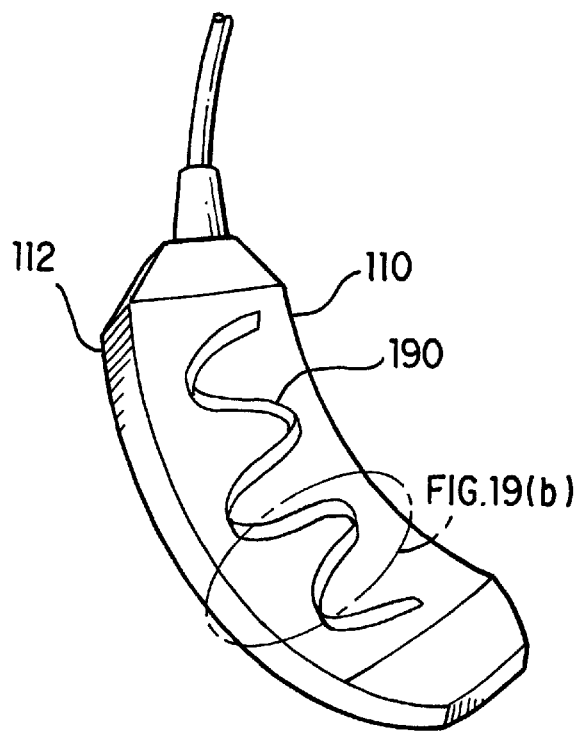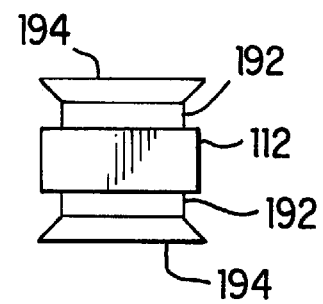
FIG.19(a)
FIG.19(b)

DENTAL CURING APPARATUS FOR LIGHT-SENSITIVE MATERIALS

CROSS REFERENCE TO RELATED APPLICATIONS

This application is a continuation-in-part application of U.S. patent application Ser. No. 09/469,923, filed on Dec. 22, 1999, now abandoned which is a divisional of Ser. No. 09/153,653, filed on Sep. 15, 1998, now U.S. Pat. No. 6,077,073, issued on Jun. 20, 2000.

BACKGROUND OF THE INVENTION

1. Field of the Invention

This invention relates to a sheathed, conformable, curing apparatus for curing light-sensitive materials such as adhesives, sealants, resins and/or whitening or coloring agents used in the dentistry and medical fields.

2. Description of Prior Art

U.S. Pat. No. 5,201,655, issued to Friedman on Apr. 13, 1993 and entitled "Optical Light Guide for Controlling the Irradiation of a Dental Restorative Material," teaches a light guide adapted for photocuring. Two optical conductors are spaced to form a gap adapted to receive a tooth. This apparatus, as disclosed, is quite bulky in design and rather frightening in appearance, especially for use in children. Furthermore, it is only adaptable to working on one tooth at a time, and hence lacks the convenience and function of a conformable multi-tooth apparatus. Additionally, without the provision of a protective barrier interposed between the apparatus and the tooth, the device is unsanitary.

U.S. Pat. No. 5,290,169, issued to Friedman, et al. on Mar. 01, 1994 and entitled "Optical Light Guide for Dental Light-Curing Lamps," discloses an optical light guide constructed of a transparent material, such as glass, acrylic, polystyrene and/or polycarbonate. FIG. 2 of the '169 patent shows how light is reflected within the light guide and directed at a tooth not using direct exposure of the light source at the treatment site. This device, too, is quite bulky in design. The device further is only adaptable to working on one tooth at a time, and hence lacks the convenience and function of a conformable multi-tooth apparatus. Additionally, without the provision of a protective barrier interposed between the apparatus and the tooth, the device is unsanitary.

U.S. Pat. No. 5,316,473, issued to Hare on May 31, 1994 and entitled "Light Curing Apparatus and Method," discloses a light-curing apparatus including a dental tray and a wand which either fits over the dental tray or is slidably engaged with the dental tray. FIGS. 2 and 3 of the '473 patent show the wand having a plurality of light sources 15, which may be a series of light bulbs or a series of light emitting diodes (FIG. 2), or which may be fiber optic element 20 having optic fibers 28 with ends 24 that emit light into an impression material. This device suffers the drawback that it relies on fiber optic light, and hence is more costly than other devices. Additionally, the apparatus is not conformable to any shape mouth or for working in conjunction with the upper and lower teeth at the same time. Moreover, without the provision of a protective barrier interposed between the apparatus and the tooth, the device is unsanitary. Furthermore, a multitude of tray and wand sizes must be manufactured to fit different mouths, making the apparatus complicated and expensive.

U.S. Pat. No. 5,415,543, issued to Rozmajzl, Jr. on May 16, 1995 and entitled "Dental Composite Curing Apparatus and Method," teaches a dental apparatus for curing actinic light curable composites, primers and adhesives. As shown in FIG. 2 of the '543 patent, nozzle 62 is centered within fiber optics tube 128, which is housed within annular conduit 150. A plurality of bores or orifices 152 are distributed about fiber optic tube 128. Gas flows out of the bores or orifices to form a uniform blanket of inert gas adjacent an emitting end of the apparatus. As shown in FIG. 1, actinic light source 20 is a visible, ultraviolet, infrared or laser light source, depending upon the type of adhesive, primer or composite to be cured. This device also suffers the drawback that it relies on fiber optic light, and hence is more costly than other devices. Additionally, the apparatus is not adaptable to working with more than one tooth at a time and is not conformable to any shape mouth for working in conjunction with more than one tooth at a time. Furthermore, without the provision of a protective barrier interposed between the apparatus and the tooth, the device is unsanitary. This device involves the use of sealed, inert gases, not solid state electro-optics. Thus, loss or leakage of the gases may occur over time.

U.S. Pat. No. 5,487,662, issued to Kipke, et al. on Jan. 30, 1996 and entitled "Dental Impression Tray for Photocurable Impression Material," teaches a dental impression tray for photocurable impression material. A light source, such as a solid state light emitter or a light emitting diode, is contained within the dental impression tray. As shown in FIG. 1, emitters 18 are positioned at spaced intervals over body 12 of the dental impression tray. FIGS. 3 and 4 of the '662 patent show different positions of emitters 18. FIG. 5 of the '662 patent shows a bank of emitters 164, such as light emitting diodes, which are used to provide light to emitters 18. This device has as a serious shortcoming no protective barrier interposed between the apparatus and the tooth. Hence, the device is unsanitary. Additionally, the apparatus is not conformable to any shape mouth for working in conjunction with both the upper and lower teeth at the same time. A variety of sizes must be manufactured to accommodate different mouth sizes.

U.S. Pat. No. 5,634,711, issued to Kennedy, et al. on Jun. 03, 1997 and entitled "Portable Light Emitting Apparatus with a Semiconductor Emitter Array," teaches a hand-held portable light emitting device for photocuring and phototherapy applications. A matrix of light emitting diodes are mounted at a front end of a housing, and emit light energy which is suitable for initiating a photo-reaction. This device, too, is quite bulky in design. Additionally, the apparatus is not adaptable to working with more than one tooth at a time and is not conformable to any shape mouth for working in conjunction with more than one tooth at a time. Also, without the provision of a protective barrier interposed between the apparatus and the tooth, the device is unsanitary. This device further requires cooling air.

U.S. Pat. No. 5,702,250, issued to Kipke on Dec. 30, 1997 and entitled "Compact Dental Impression Tray for Photocurable Impression Material," discloses a dental impression tray that has an array of solid state light emitters for curing photocurable impression material received in a channel of the tray. As shown in FIG. 2 of the '250 patent, emitters 32, such as light emitting diodes, are positioned to emit light to the impression material. This device has as a serious shortcoming no protective barrier interposed between the apparatus and the tooth. Hence, the device is unsanitary. Additionally, the apparatus is not conformable to any shape mouth for working in conjunction with more than one tooth at a time, and does not permit light exposure simultaneously to the right and left sides of the mouth.

U.S. Pat. No. 5,711,665, issued to Adam, et al. on Jan. 27, 1998 and entitled "Method and Apparatus for Binding Orthodontic Brackets to Teeth," teaches a method and a device to bond orthodontic brackets to teeth. A curing light is removably received within a passage of the bracket. This device is quite bulky in design and has no protective barrier interposed between the apparatus and the tooth. Designed more for use with braces, the device is unsanitary insomuch as repeated, direct contact between the device and the mouth is expected. Additionally, the apparatus is not conformable to any shape mouth for working in conjunction with more than one tooth at a time. The key/keyhole design and use makes the method difficult to employ, requiring laborious skill in placement for each tooth.

U.S. Pat. No. 5,718,577, issued to Oxman, et al. on Feb. 17, 1998 and entitled "Dental Impression Tray with Chemiluminescent Light Source," teaches a dental impression tray that forms a channel which receives or contains a photocurable dental impression material. A wall or a wall portion adjacent the chamber is constructed of a material that transmits electromagnetic actinic radiation. Another chamber of the tray contains a chemiluminescent composition that cures the photocurable dental impression material. The device relies on a chemical reaction to produce the light used during the cure instead of direct illumination with solid state electro-optics. Additionally, the apparatus is not conformable to any shape mouth; hence, different sizes must be manufactured to accommodate a variety of mouth sizes. Furthermore, the device is most adaptable for working in conjunction with one tooth at a time; it cannot be accommodated to work on both the upper and lower teeth simultaneously. Furthermore, without the provision of a protective barrier interposed between the apparatus and the tooth, the device is unsanitary.

Thus, a problem associated with dental curing apparatus for light-sensitive materials that precede the present invention is that many of them are bulky in design, and hence cumbersome to use.

Yet another problem associated with dental curing apparatus for light-sensitive materials that precede the present invention is that many of them are hand-held, and hence difficult to use with precision. The medical/dental professional, an assistant or the patient himself may be required to stabilize the apparatus during its entire placement time in the patient's mouth.

A problem associated with dental adhesive-curing apparatus that precede the present invention is that many of them are only adaptable to working on one tooth at a time, and hence do not facilitate rapid working conditions during dentistry.

Yet an additional problem associated with dental curing apparatus for light-sensitive materials that precede the present invention is that many of them are frightening in appearance, and hence susceptible to consumer rejection. Children, especially, may be averse to bulky equipment.

Another problem associated with dental curing apparatus for light-sensitive materials that precede the present invention is that many of them are chemically activated, in that many of them rely on light produced from a chemical reaction for their efficacy. Calibration of this equipment may be needed to correct for leakage or depletion of gases over time.

Still a further problem associated with dental curing apparatus for light-sensitive materials that precede the present invention is that many of them are expensive to manufacture and use, particularly where a multiplicity of sizes is required.

Yet an additional problem associated with dental curing apparatus for light-sensitive materials that precede the present invention is that many of them must be reused in their entirety to be cost effective. Where a multiplicity of sizes is required, the medical/dental office is faced with the prospect of stocking many such apparatus, concomitantly driving up the cost of using such apparatus.

Still a further problem associated with dental curing apparatus for light-sensitive materials that precede the present invention is that many of them rely on fiber optic light, and hence are perhaps more costly than other devices. These are not self-contained in a small package. Furthermore, these may rapidly generate harmful levels of heat at the light source, requiring indirect illumination.

Yet an additional problem associated with dental adhesive-curing apparatus that precede the present invention is that many of them are designed essentially for use with dental braces or brackets.

Another problem associated with dental curing apparatus for light-sensitive materials that precede the present invention is that they lack the appearance of being sanitary, and hence are even more susceptible to consumer rejection and may contribute to the spread of infection by cross-contamination. Additionally, their design does not permit ease of total sanitation of all parts, particularly those that are difficult to access during the sanitation process.

An even further problem associated with dental adhesive-curing apparatus that precede the present invention is that they are not conformable to any shape mouth for working in conjunction with the upper and the lower teeth at the same time.

For the foregoing reasons, there has been defined a long felt and unsolved need for a dental curing apparatus for light-sensitive materials, particularly as adapted in the field of dentistry, that is sterile in fact, sanitary in appearance and hence perceived to be sterile, easily placed in the mouth, inexpensive to manufacture and adjustable to accommodate a variety of differently shaped mouths and bites such that a single design can be accommodated to all persons to which it is adapted. Such a device should be self-contained with minimal parts. It should be able to be used to treat as many teeth as maximally possible at the same time, thereby reducing overall treatment time, complexity and expense.

In contrast to the foregoing, the present invention constitutes a dental curing apparatus for light-sensitive materials that seeks to overcome the problems discussed above, while at the same time providing a simple, easily constructed apparatus that is readily adapted to a variety of applications, most particularly those in the field of dentistry.

SUMMARY OF THE INVENTION

A device for curing adhesives, sealants and/or whitening or coloring agents used in the medical/dentistry field is disclosed. In one preferred embodiment of this invention, light energy is provided to cure light-sensitive materials. The light energy source can be housed within a clear, a transparent and/or a translucent housing. The housing is constructed of a material that may have optical qualities to enhance the light curing performance. The housing is preferably sealed. The housing can be constructed of a solid, such as a poured resin, or can be constructed as a hollow structure. The housing preferably has a shape with an overall curve that conforms to an approximate shape of dentition, particular variants of which are selectable depending upon the precise application desired. The housing can also be constructed as a flexible material, including a flexible material that has shape memory characteristics. The housing can be mounted within a disposable oversertion sheath, for sterility purposes. During use, the light source is transmitted to cure the adhesives, sealants and/or whitening or coloring agents.

Apparatus of the prior art generally can be bulky and frightening in appearance, leading to consumer rejection. Additionally, these can be unsanitary for multiple use. Many of these apparatus are not adaptable for use in more than one patient. Impression trays of prior patients must be processed for dental casts after removal from the mouth, limiting use to once per placement. Unlike these apparatus, the present invention is therefore compact in design, sanitary for multiple use, and adaptable for use in more than one patient. Impression trays of prior patients need not be processed for dental casts after removal from the mouth, thus permitting more than one use per placement. The apparatus can be use to cure or expose light to several different teeth simultaneously, including upper, lower, right and left sides if maintained across the dentition to transverse the tongue.

It is therefore an object of the present invention to provide a dental curing apparatus for light-sensitive materials that is not bulky in design.

Still another object of the present invention is to provide a dental curing apparatus for light-sensitive materials that does not need to be hand-held or rigidly stabilized during use.

Yet another object of the present invention is to provide a dental adhesive-curing apparatus that is adaptable to working on more than one tooth at a time in the same jaw or in opposing jaws simultaneously.

It is a further object of the present invention to provide a dental curing apparatus for light-sensitive materials that has a patient-friendly, non-invasive appearance.

Still another object of the present invention is to provide a dental curing apparatus for light-sensitive materials that is not chemically activated.

Yet another object of the present invention is to provide a dental curing apparatus for light-sensitive materials that is inexpensive to manufacture and use.

Another object of the present invention is to provide a dental curing apparatus for light-sensitive materials that is largely reusable while yet preserving its sterility.

Still a further object of the present invention is to provide a dental curing apparatus for light-sensitive materials that does not rely on fiber optic light.

Yet another object of the present invention is to provide a dental adhesive-curing apparatus that is not designed essentially for braces or brackets, but rather is designed for specific applications located on many teeth at the same time.

An even further object of the present invention is to provide a dental curing apparatus for light-sensitive materials that is sanitary and also conveys the appearance of being sanitary.

Still a further object of this invention is to provide a dental adhesive-curing apparatus that is conformable to any shape mouth for working in conjunction with more than one tooth at a time.

These and other objects, advantages and features of the present invention will be apparent from the detailed description that follows.

DESCRIPTION OF THE DRAWINGS

In the detailed description that follows, reference will be made to the following figures:

FIG. 10 illustrates an upper, perspective view of a portion of a preferred embodiment of the apparatus.

FIG. 11 illustrates an upper, perspective view of a portion of a preferred embodiment of the apparatus.

FIG. 12 illustrates a side view of a preferred embodiment of the apparatus shown in FIG. 11.

FIG. 19 illustrates an upper, perspective view of an embodiment of a dental adhesive-curing apparatus and a side, cross-sectional view of a portion thereof.

DETAILED DESCRIPTION OF THE PREFERRED EMBODIMENTS

Figure 1:
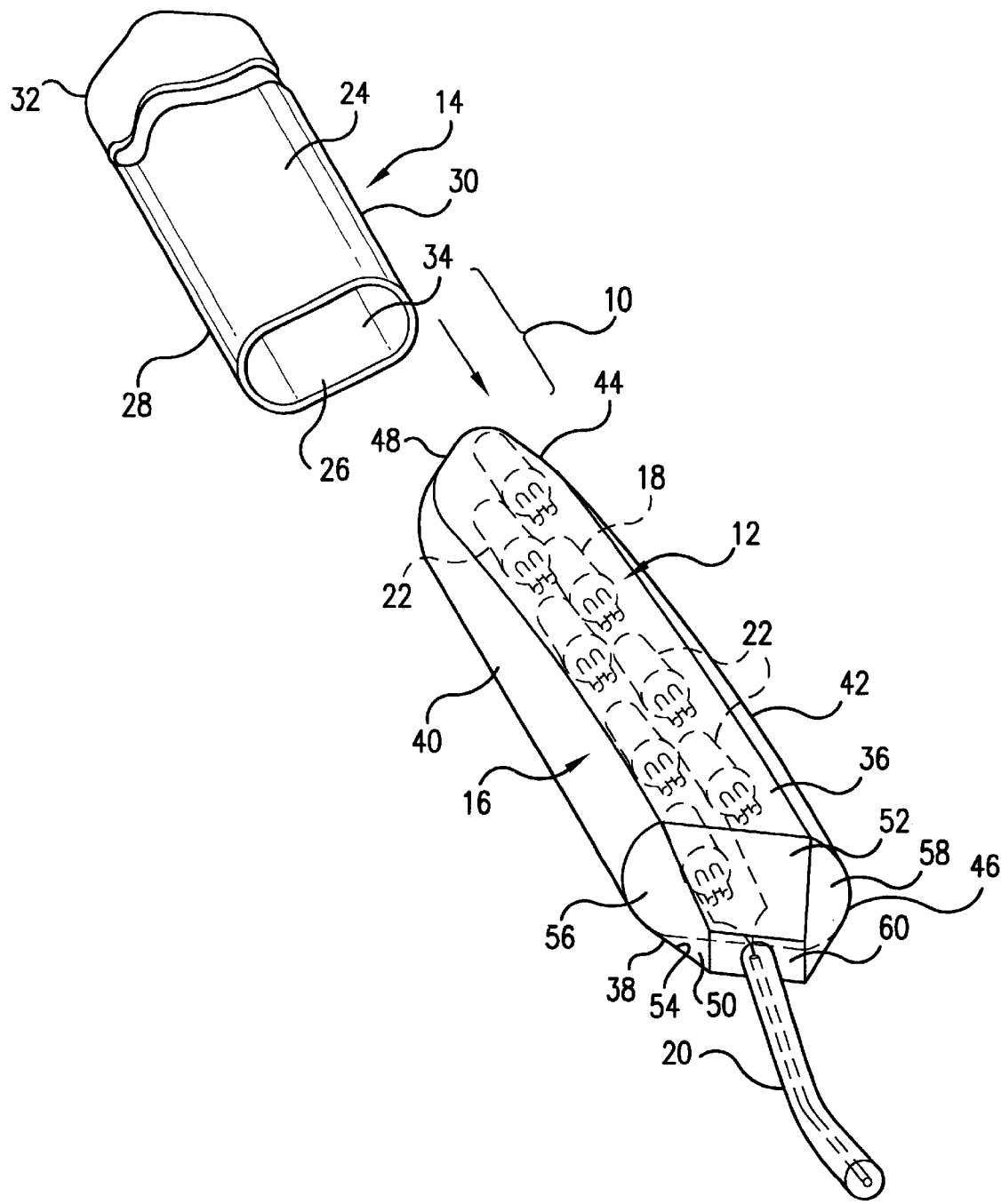
FIG. 1 illustrates an upper, perspective view illustrating a preferred embodiment of the light emitting diode-array light apparatus for curing adhesives, sealants and/or whitening or coloring agents used in the dentistry field.

FIG. 1 illustrates a first embodiment of the conformable, multi-tooth dental curing apparatus 10 constructed and arranged to be received in a human mouth. As constructed, the conformable, multi-tooth curing apparatus 10 comprises a reusable curing section 12 and a disposable sanitary oversertion sheath 14. The curing section 12 has a housing 16. A light source 18 for curing the adhesive is provided by an LED array 18 contained within the housing 16 so as to be maintained in non-contacting relation with the human mouth. A power supply 20 (to transformer or battery supply, not shown) provides power to individual LED's 22 that are arranged to make up the LED array 18.

Thus, as illustrated, the curing section 12 is reusable, and has an overall length of more than about one inch. The housing 16 has a generally flattened, elongated shape. The oversertion sheath 14 is disposable and also has a generally flattened, elongated shape. The oversertion sheath 14 is constructed and arranged so as to receive the housing 16, and the housing 16 is likewise constructed and arranged so as to be insertable into the oversertion sheath 14.

Referring now in more detail to the construction of the sanitary oversertion sheath 14, a flat sheath top 24 and a flat sheath bottom 26 are joined by opposed, semicylindrical sheath sides 28, 30 to form a generally flattened tubular shape constructed and arranged to receive the curing section 12. A tapered sheath end 32 defines one end of the housing 16, and a housing receiving aperture 34 is provided at the opposite end. The sanitary oversertion sheath 14 is preferably constructed of a deformable, resilient plastic or elastomer so that it can be conformed to the shape of the human mouth into which it is to be inserted, thereby permitting deformation to the shape of the natural dentition. The sanitary oversertion sheath 14 preferably has a thickness of between 0.1 mm and 2.0 mm, although it is understood that the thickness is selected to optimize sheath strength versus sheath flexibility and light penetration.

Likewise, referring to the curing section 12 in more detail, the housing 16 is constructed and arranged as follows. The housing 16 is provided with a flat housing top 36 and a flat housing bottom 38. Two opposed, semicylindrical housing sides 40, 42 are interposed between the flat housing top 36 and bottom 38, thus defining a generally flattened columnar shape of the housing 16.

The housing 16 is provided with an insertion end 44, oriented toward the inside of the human mouth to which it is inserted, and a power receiving end 46 for receipt of the power that facilitates curing of a dental compound. The insertion end 44 is generally shaped into a bow shaped tapered contour 48. The power receiving end 46 is generally shaped into a beveled power receiving end taper 50, having a trapezoidal top taper 52 and a trapezoidal bottom taper 54, each connected on opposite sides by a pair of frustroconical side sections 56, 58. Due to the orientation of the trapezoidal tapers 52, 54 and the frustroconical side sections 56, 58, a rectangular power receiving end face 60 terminates the beveled power receiving end taper 50. The rectangular power receiving end face 60 receives positive feed 62 and negative return 64.

The housing 16 is preferably constructed of a transparent or translucent, deformable, resilient plastic or elastomer so that it can be conformed to the shape of the human mouth into which it is to be inserted, thereby permitting deformation to the shape of the natural dentition.

The inner dimensions of the sanitary oversertion sheath 14 are selected so as to substantially correlate with the outer dimensions of the housing 16, allowing just enough tolerance to facilitate practicable removal and insertion of the sanitary oversertion sheath 14 and yet permit a sufficiently snug fit so as to effect retention of the sanitary oversertion sheath 14 on the housing 16. The length of the sanitary oversertion sheath 14 is selected to approximately coincide at least with the effective length of the curing section 12.

The housing 16 is constructed and arranged so as to be substantially sealed. The sanitary oversertion sheath 14 is constructed and arranged so as to be disposable, that is, materials are selected so as to minimize the production costs of the sanitary oversertion sheath 14.

Figure 2:
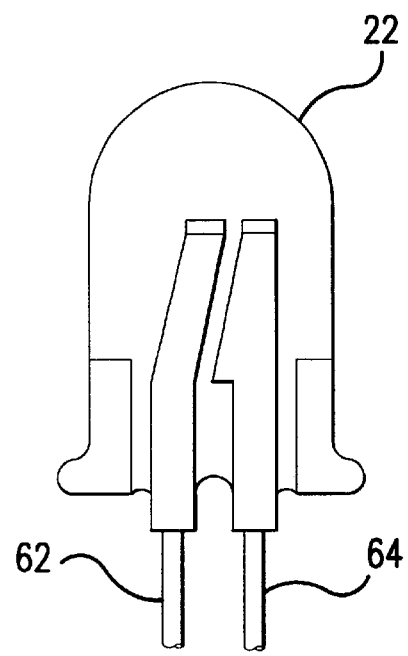
FIG. 2 illustrates a schematic view illustrating a light emitting diode as adapted for use with the light emitting diode-array light apparatus for curing adhesives, sealants and/or whitening or coloring agents used in the dentistry field.
Figure 3:
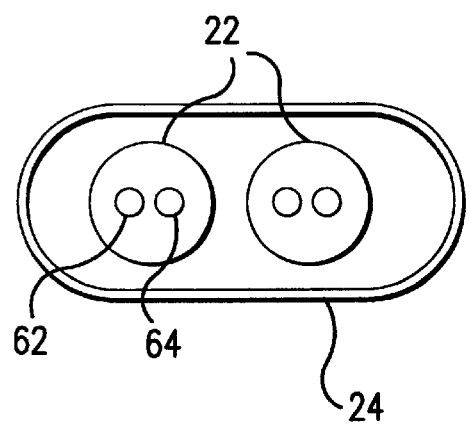
FIG. 3 illustrates a top plan view of a light emitting diode as adapted for use with the light emitting diode-array light apparatus for curing adhesives, sealants and/or whitening or coloring agents used in the dentistry field.

Referring now to FIGS. 2 and 3, LED 22 is provided a positive feed 62 and a negative return 64. In the preferred embodiment, power is supplied in the form of a 5 volt, direct current power supply from a transformer (not shown). However, it is understood that selection of the desired voltage and current type is dynamic, and that any voltage low enough to be safe but high enough to be effective may be used. Moreover, where light energy is to be used to effect curing, sufficient light energy is supplied to cure light sensitive materials, such as sealants.

Figure 4:
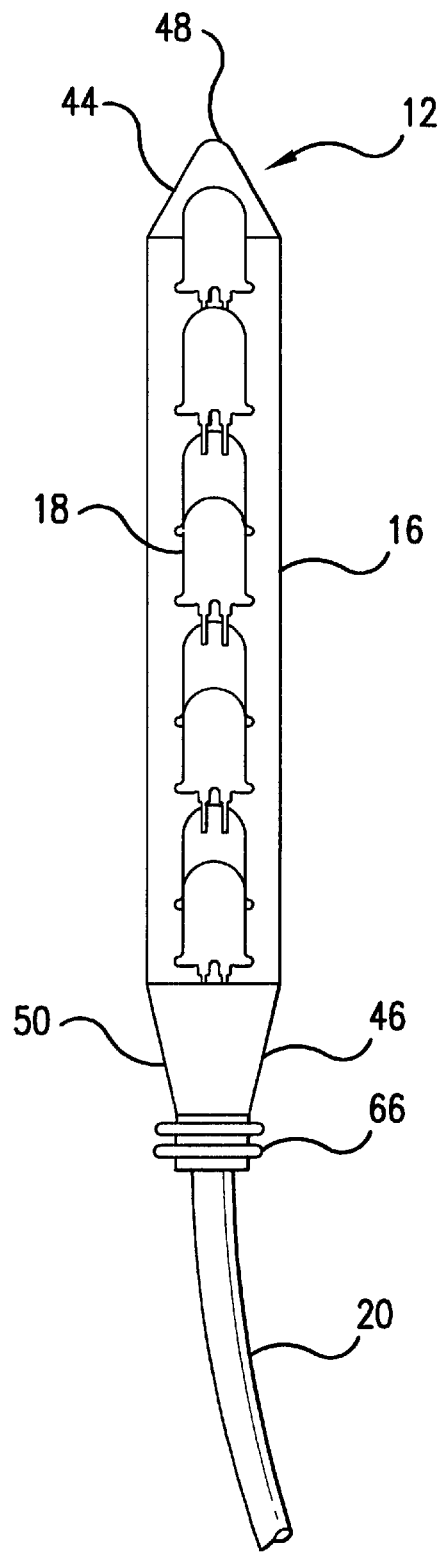
FIG. 4 illustrates a side cut-away view of a preferred embodiment of the light emitting diode-array light apparatus for curing adhesives, sealants and/or whitening or coloring agents used in the dentistry field.
Figure 5:
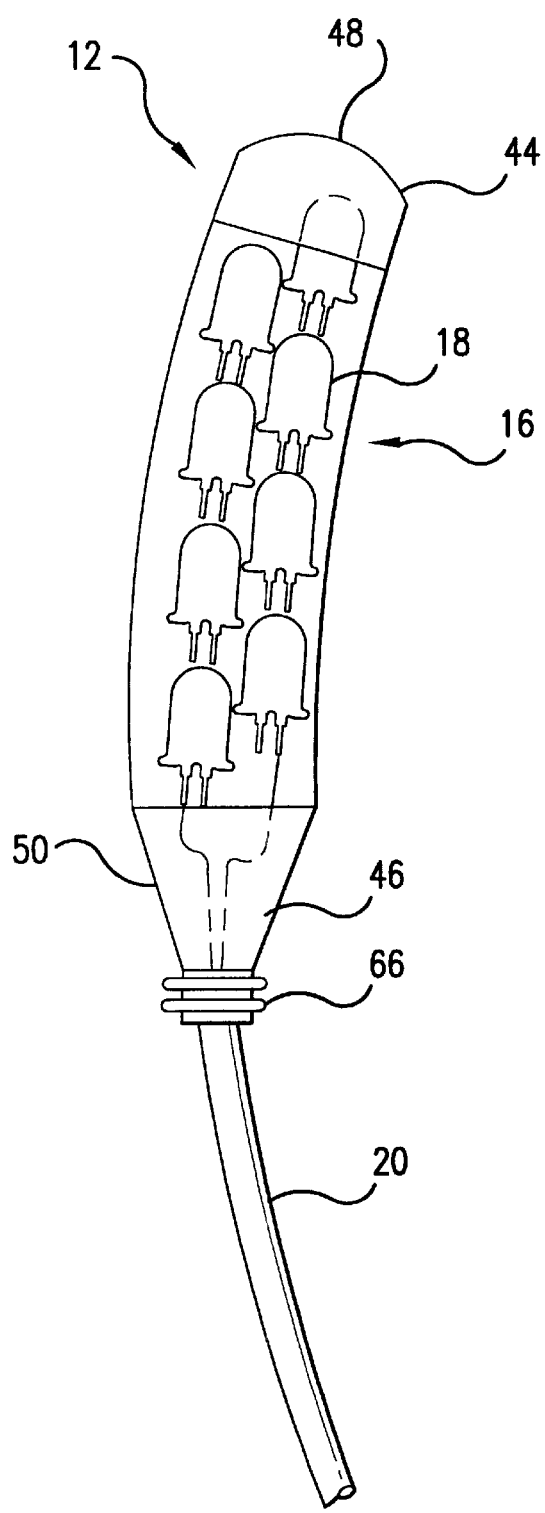
FIG. 5 illustrates a top plan cut-away view of the light emitting diode-array light apparatus for curing adhesives, sealants and/or whitening or coloring agents used in the dentistry field shown in FIG. 4.

Referring now to FIGS. 4 and 5, the housing 16 is shown in cross-sectional, cutaway view. As seen from the side, in FIG. 4, the housing 16 is provided with a flexible, corrugated, protective collar 66 that protects the power supply 20 from being broken or compromised, leading to better reliability during multiple use. The LED's 22 are imbedded in the housing 16. In the preferred embodiment, the LED array 18 is connected in parallel, although connection in serial is foreseen, as well.

Figure 6:
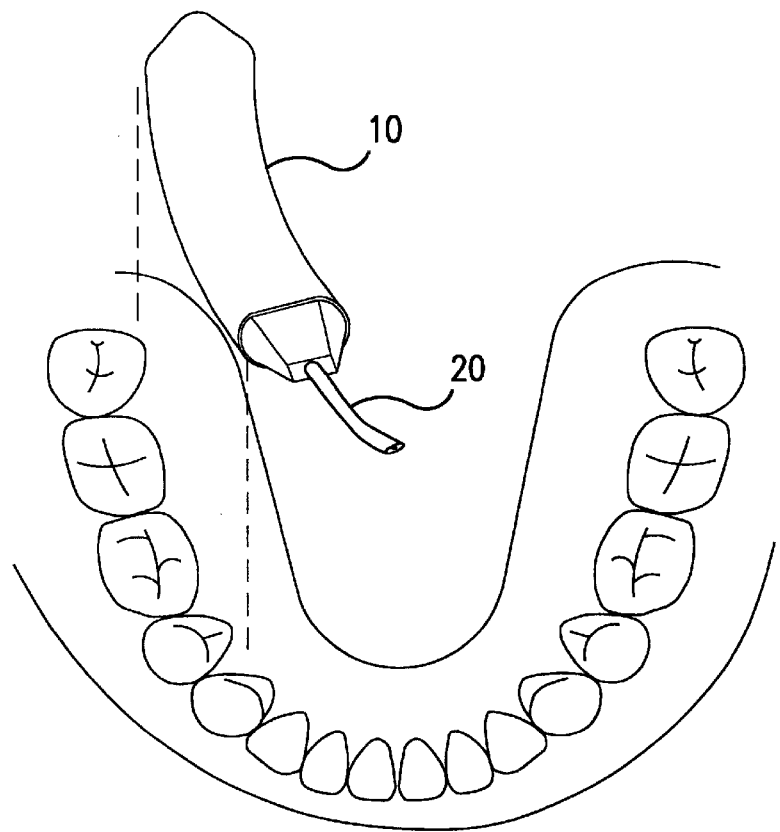
FIG. 6 illustrates a top cut-away view of the light emitting diode-array light apparatus for curing adhesives, sealants and/or whitening or coloring agents used in the dentistry field as shown in FIG. 4 as positioned in a human mouth.
Figure 7:
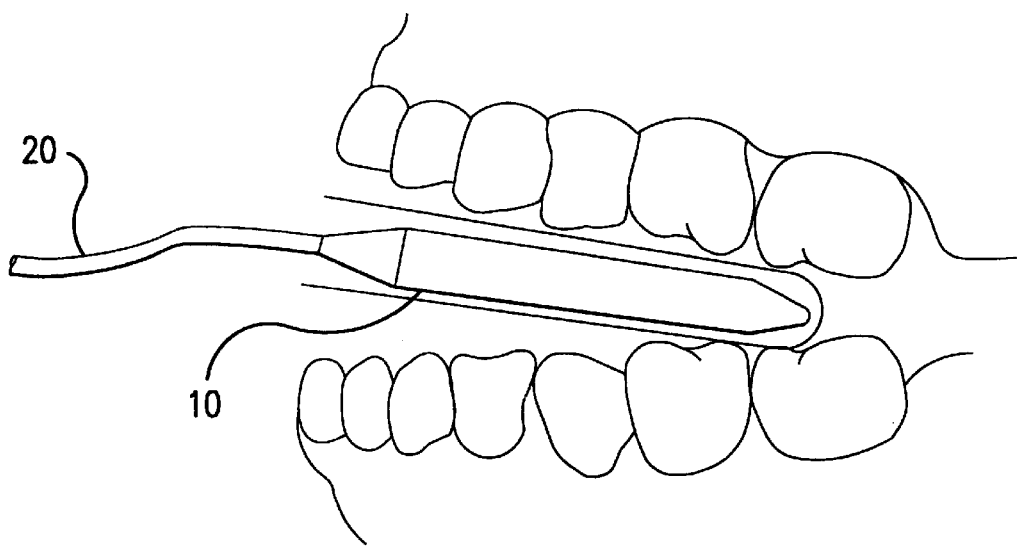
FIG. 7 illustrates a side cut-away view of the light emitting diode-array light apparatus for curing adhesives, sealants and/or whitening or coloring agents used in the dentistry field as shown in FIG. 4 as positioned in a human mouth.

As shown in FIGS. 6 and 7, the conformable, multi-tooth curing apparatus 10 is bent into or manufactured to conform to the shape of natural dentition specific to the particular patient to be treated. Once adhesives, sealants or whitening agents have been inserted into the desired locations within the patient's mouth, the conformable, multi-tooth curing apparatus 10 is placed in the human mouth. Power is supplied to the LED array 18 so that curing is effected.

Figure 8:
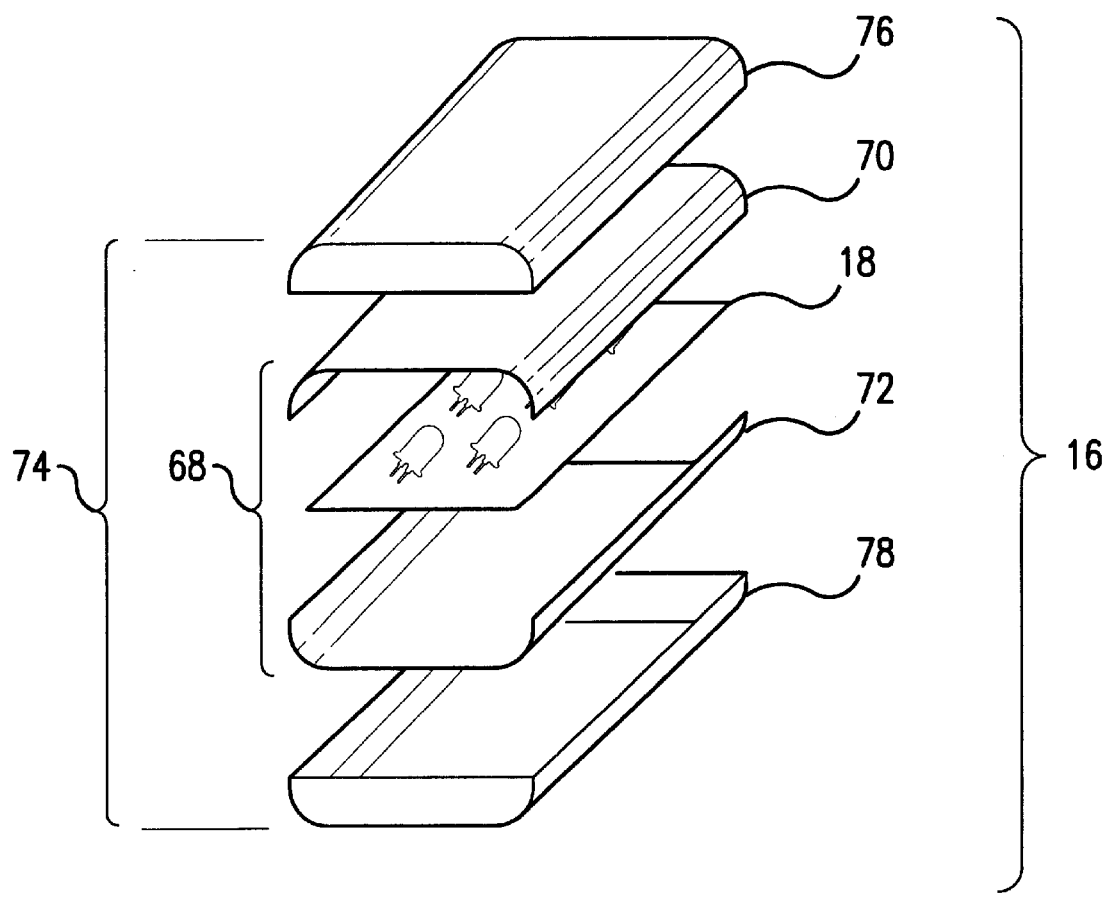
FIG. 8 illustrates an exploded, perspective view of a portion of a preferred embodiment of the apparatus.
Figure 9:
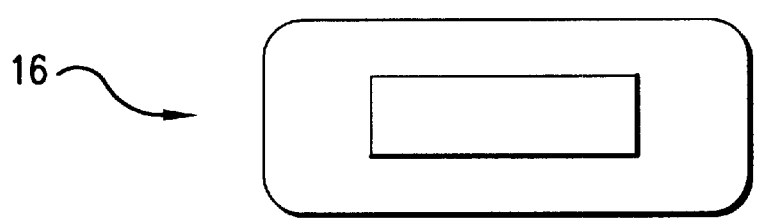
FIG. 9 illustrates a frontal plan view of the apparatus shown in FIG. 8.

FIG. 8 illustrates an exploded view of yet another embodiment of the housing 16. Here, the LED array 18 is contained within a diffuser grid 68 comprising two diffuser grid halves 70, 72. The diffuser grid 68 is, in turn, contained within an outer shell 74 comprising a pair of outer shell halves 76, 78. FIG. 9 illustrates a front view of the housing 16 shown in FIG. 8. The housing 16 is approximately ¾ inches wide and 5/16 inches high.

In alternative embodiments, the array 18 can be constructed of materials other than standard LED, such as organic light emitting diodes (OLED), liquid crystal displays (LCD), printed circuit board (PCB) units or, potentially, PCB units equipped with discrete surface-mounted technology (SMT) opto-electronic devices, lamp or other LED units, thereby facilitating the emission of multi-directional energy patterns. Supplemental accessory LEDs may also be positioned in proximity to the main opto-electronic unit for directional point curing. The OLED may be flexible, as has been proposed by OLED manufacturers such as Universal Display Corporation. Flexible PCB units are available from Dynamics Research Corporation, among other sources. Alternatively, grid halves 70, 72 can be Fresnel lens sheets integrated into the housing 16 to further enhance the opto-electric properties of the apparatus. Thus, dental curing apparatus with capabilities to cure light-sensitive dental materials on both upper and lower teeth simultaneously, and the left and right side of the mouth at the same time, and/or, directionally for forward-point curing material on a specific tooth, or portion of a tooth, is further facilitated.

FIGS. 10 through 12 illustrate additional perspective views of the preferred embodiment shown in FIG. 8. The LED array 18 is shown in FIG. 10. FIG. 11 shows the curing section 12 from a top perspective view. FIG. 12 illustrates a side view of the curing section 12. The curing section as shown is approximately 3 inches long.

Figure 13:
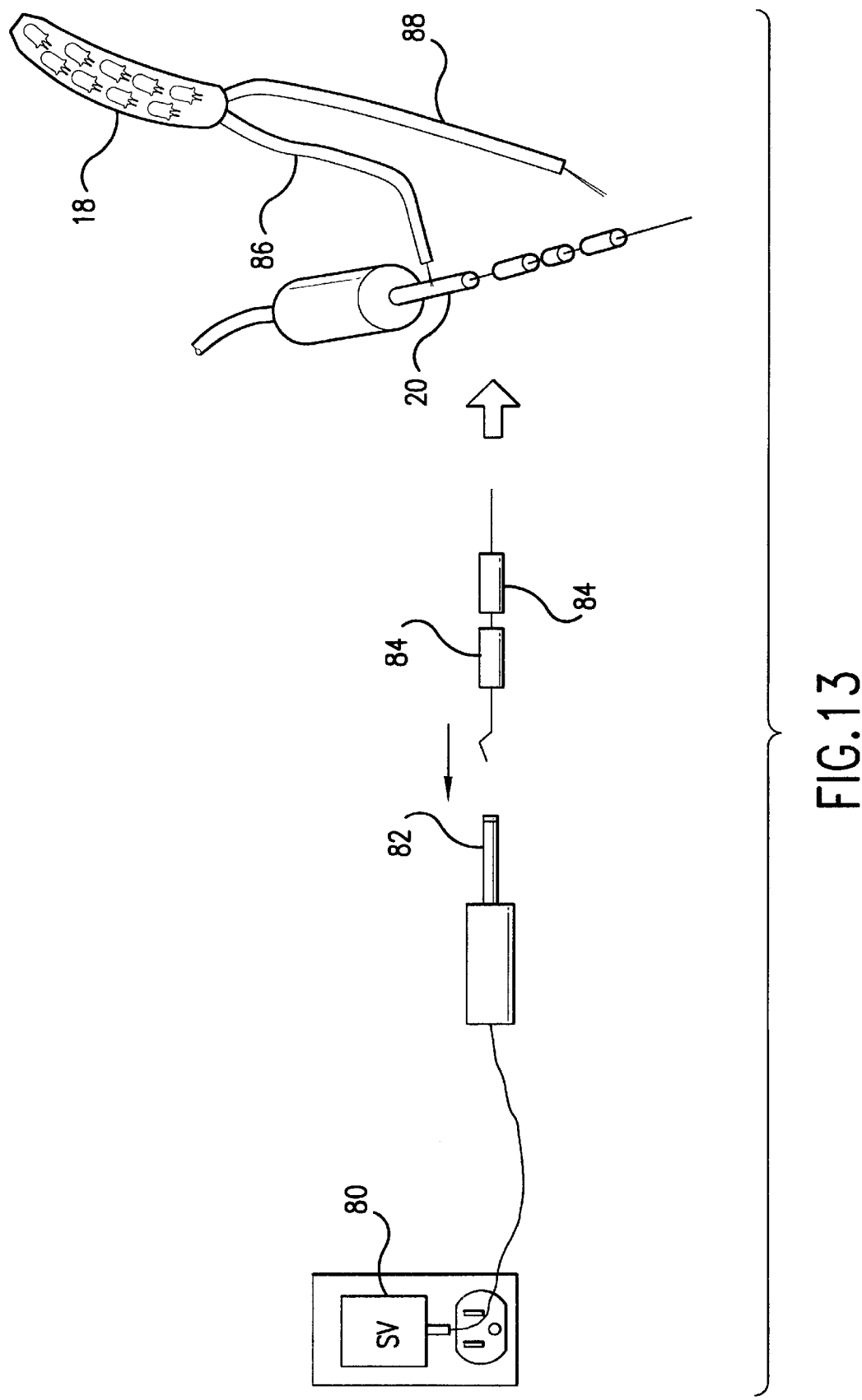
FIG. 13 illustrates a side perspective view of the light emitting diode-array light apparatus for curing adhesives, sealants and/or whitening or coloring agents used in the dentistry field as assembled for use in the field.

FIG. 13 illustrates use of the apparatus. In this particular embodiment, the transformer 80 connects to a 110 volt, AC power supply and provides a 3 volt, DC power supply to the apparatus 10. A DC power plug 82 is connected to a series of resistors 84, each having approximately 100 ohms of resistance, to provide the desired amperage. A red lead 86 and a black lead 88 are connected to the apparatus 10. By touching the leads 86, 88 to the power supply 20, electricity is conducted through the LED array 18 to effect curing of the dental compound to be cured.

Thus, the LED position and conductor arrangement, with the anode and cathode separated on opposing sides of a opto-electronic board, is illustrated. The opto-electronic board may have lens and/or light diffusing properties. As illustrated, the LED units are connected in parallel. The board is preferably constructed of a stamped or molded transparent, temperature-resistant, electrically insulating material, such as Dupont Corporation's Mylar and/or may comprise light reflecting material as in white masked or screened PCB.

The circuit pattern can be etched or otherwise embedded into the opto-electronic board. To fully encase the completed array, the board can be implanted in a mold which is then filled with a electrically neutral resin or urethane. This is then sealed within two pre-molded half sections to fully enclose the board. Additional holes or pegs may be provided in the opto-electronic board for ease in aligning the board in the casing and stabilizing its position.

The lens/casing could be molded from 94V-0 compliant polycarbonate, which would also assure maximum light transmission and increased protection from ESD. Alternatively, Lexan or Lucite may also be used. Surrounding the array with a resin and mold can be accomplished by using an electrically neutral, clear, self-curing resin such as 3M Corporation's DP-270 two-component system. Other alternatives are W.R. Grace and Company's Stycast 1267 Epoxy Encapsulant, Conap Corporation's Conathane UC53 urethane, or encapsulating or potting compounds for medical or dental use, such as Epoxy Technology 300 Series, Epoxy Etc. 20-3238.

In an alternative embodiment, stainless steel wire is braided over each LED lead and crimped in position. Two separate housing halves were created using balsa patterns and vacuforming equipment. The optoelectronic board was placed between the halves, which were heat annealed together. The apparatus is transparent.

Alternative sources of light are also provided. For example, alternative arrangements and orientations of LED bulb units with or without opto-electric board can be provided. The LED array may be supported by soldered leads (anode to anode, cathode to cathode) in series/parallel combination. In between bulb LED units, surface mount LED units may be fixed to various locations on opto-electric board, or to inside housing shell for additive effect of curing.

A device 10 for curing adhesives, sealants and/or whitening or coloring agents used in the dentistry field is therefore described. The LED array 18 is connected, preferably but not necessarily in parallel. A relatively low voltage source, such as one having about 5 volts, delivered from a transformer, powers the LED array 18. The LED array 18 is protected within a clear, a transparent and/or a translucent housing 16. The housing 18 is sealed. The housing 18 can be constructed of a solid, such as a poured resin, or can be constructed as a hollow structure.

The housing 18 has a shape with an overall curve that conforms to an approximate shape of dentition. In the preferred embodiment as thus described, the housing 18 is constructed as a flexible material, including a flexible material that has shape memory characteristics. The housing 18 is mountable within a disposable oversertion sheath 14, for sterility purposes. During use, the LED array 18 transmits light which cures the adhesives, sealants and/or whitening or coloring agents, preferably on several teeth simultaneously.

In FIG. 14, alternative embodiments of a dental curing apparatus for light-sensitive materials are shown. Utilizing many of the features, details and dimensions described in the foregoing and illustrated in FIGS. 1 through 13, the pertinent differences can be described as follows.

Shown in FIG. 14 as a dental adhesive-curing apparatus 110, the apparatus 110 can be shaped in varying ways to accommodate a variety of contours. FIG. 14 illustrates the dental curing apparatus 110 having alternatively-shaped curing sections 112. By describing the various shapes or contours of curing sections 112, it is understood that these can be obtained either by selecting the appropriately shaped housing or oversection sheath. Generally, it has been found that a preselected shape or contour of oversection sheath provides the desired shape or contour of curing section 112. These curing sections 112 possess optical lens/focusing/diffusing properties for optimal light distribution or radiation, and facilitate optimal positioning within the mouth to accommodate varying oral anatomy.

Figure 14A:
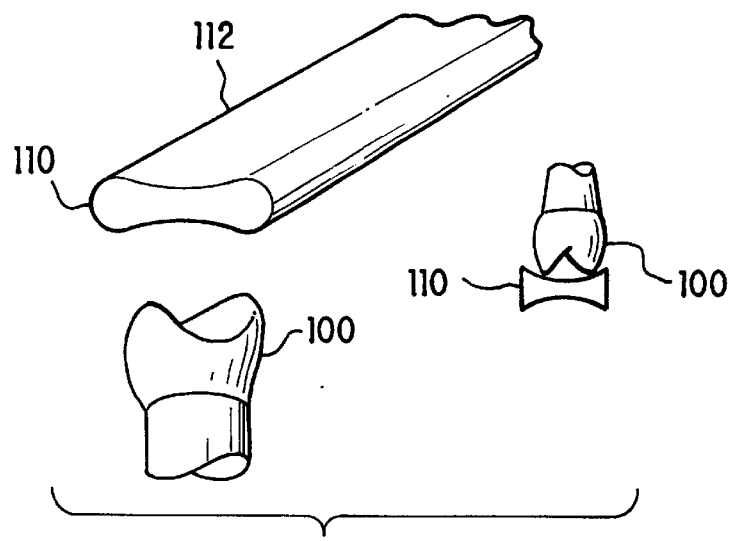
FIG. 14 illustrates an upper, perspective view of alternative embodiments of a dental adhesive-curing apparatus.
Figure 14B:
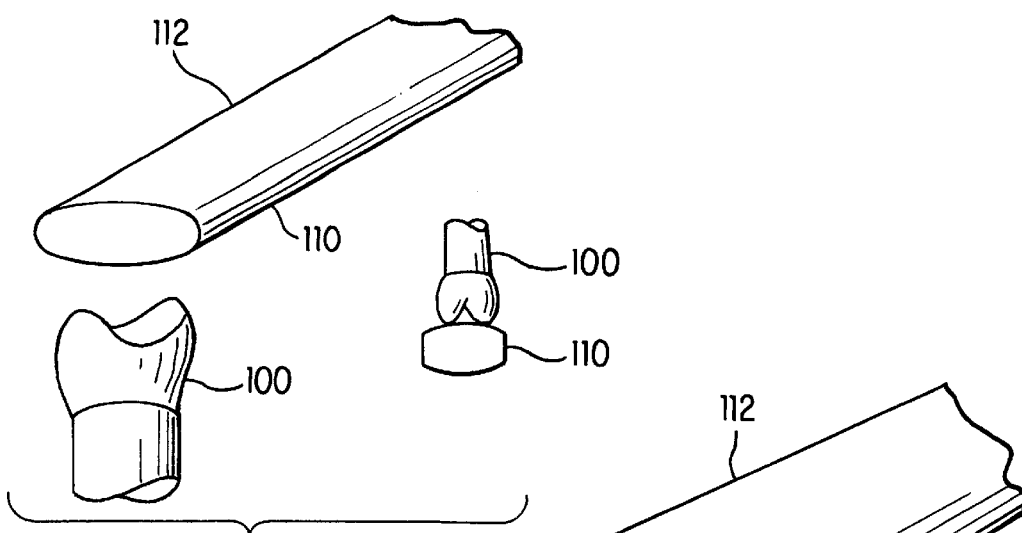
Figure 14C:
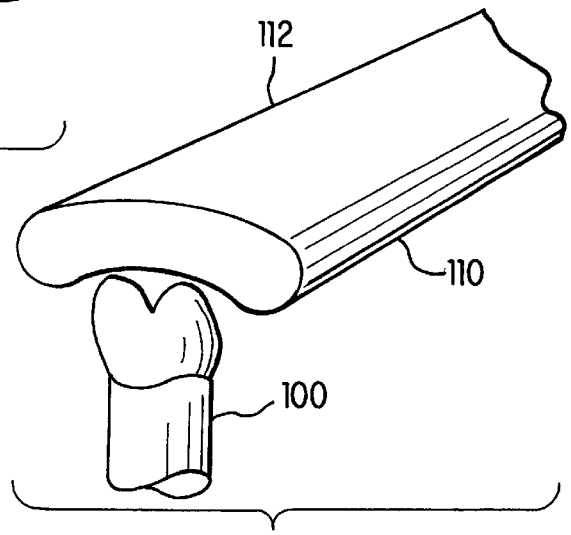

For example, FIG. 14(a) shows a generally concave curing section 112, FIG. 14(b) shows a generally convex curing section 112 and FIG. 14(c) shows a curing section 112 having a convex side and a concave side. Each of these is uniquely contoured to complement differing contours of a tooth 100.

Figure 15:
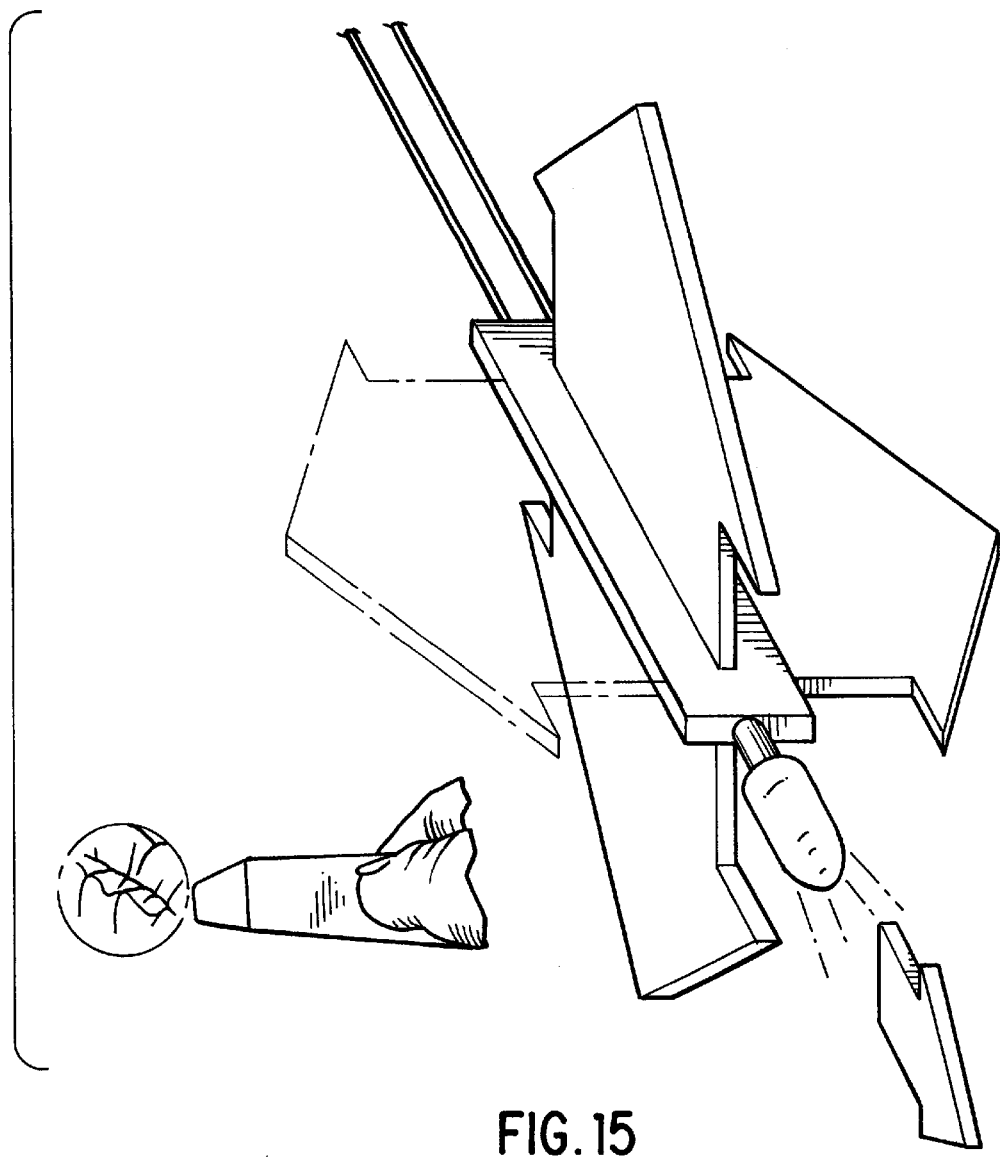
FIG. 15 illustrates a schematic view illustrating an alternative embodiment of a dental adhesive-curing apparatus.

As earlier described in connection with FIG. 9, embodiments constructed with an OLED, LCD, PCB equipped with discrete SMT opto-electronic devices, lamp or other LED units can be constructed and arranged to facilitate multi-directional emission of light. This can facilitate point curing, as shown generally in FIG. 15. Applications of this apparatus include curing light sensitive border molding materials to facilitate denture impressions. Point curing can be used outside the mouth, as well, to bench cure light sensitive materials.

Figure 16A:
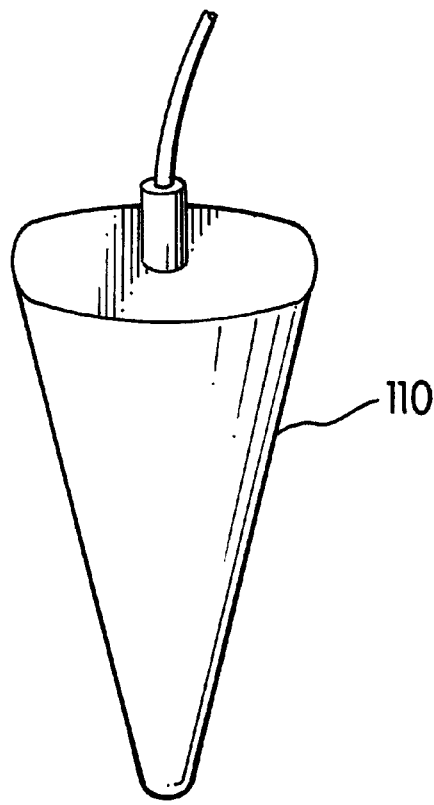
FIG. 16 illustrates an upper, perspective view of alternative embodiments of a dental adhesive-curing apparatus.
Figure 16B:
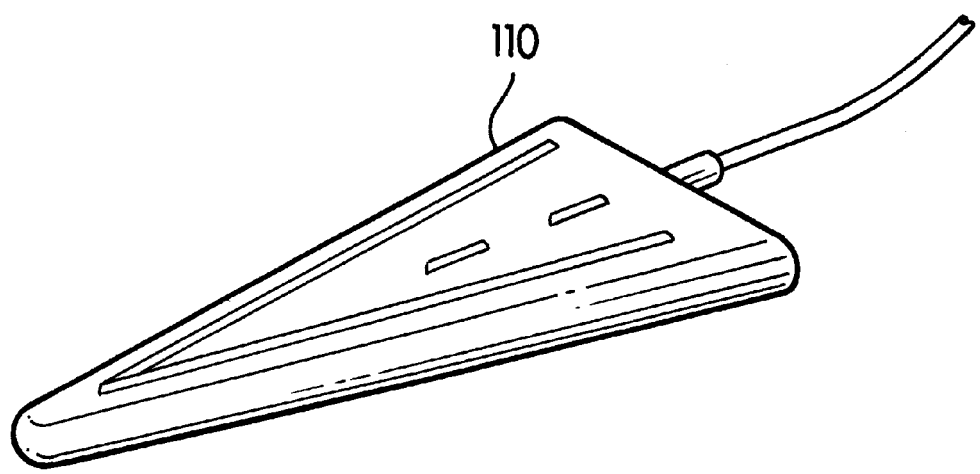
Figure 17C:
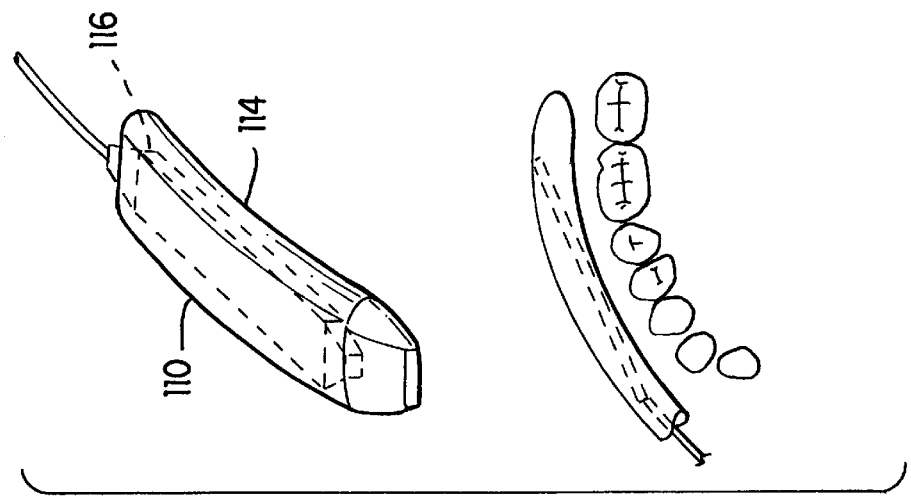
FIG. 17 illustrates an upper, perspective view of alternative embodiments of a dental adhesive-curing apparatus illustrating their use in a human mouth.
Figure 17B:
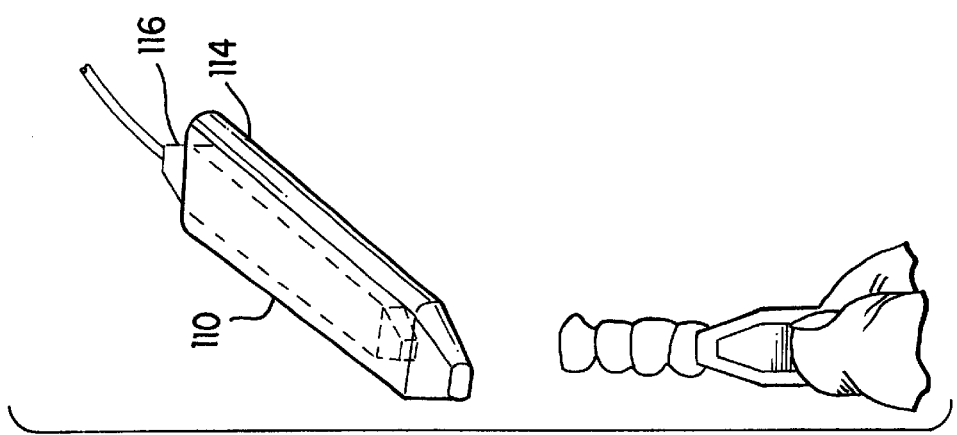
Figure 17A:
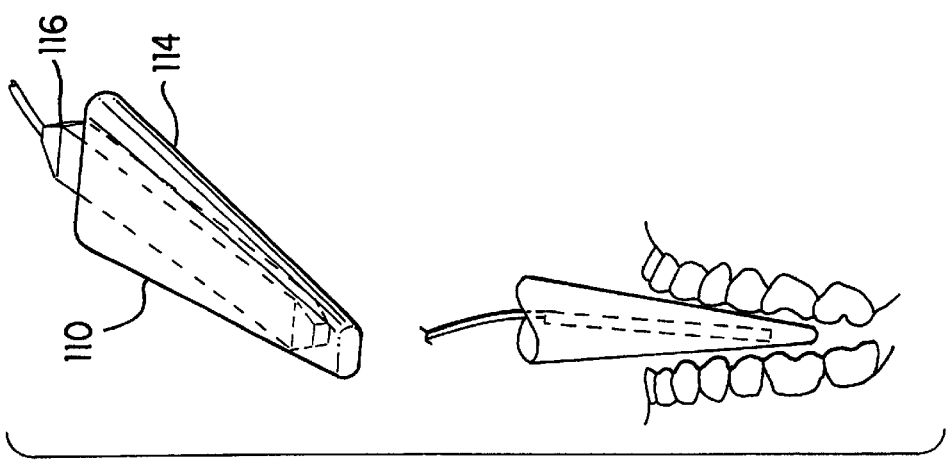
Figure 18A:
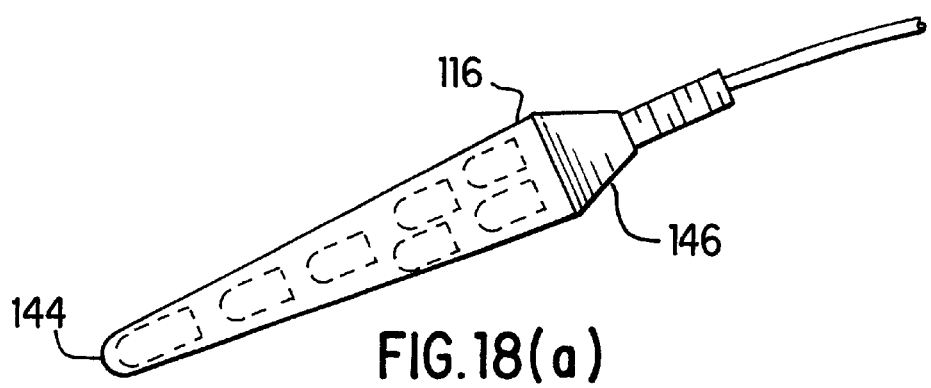
FIG. 18 illustrates an upper, perspective view of an embodiment of a dental adhesive-curing apparatus illustrating its use in a human mouth.
Figure 18B:
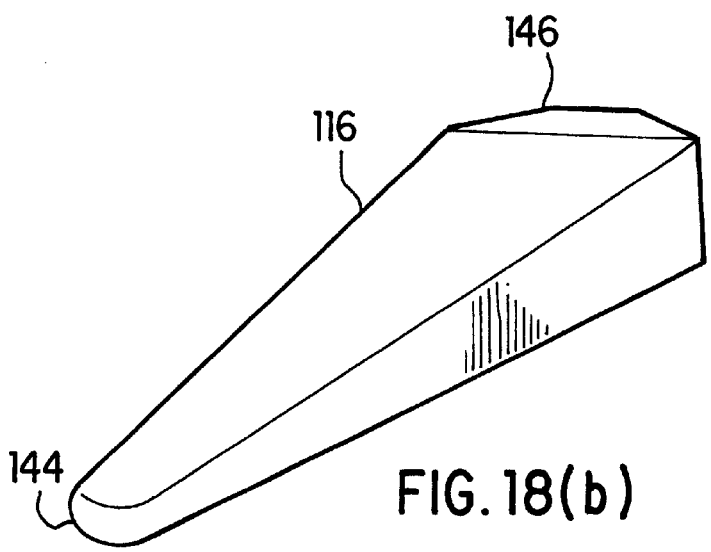
Figure 18C:
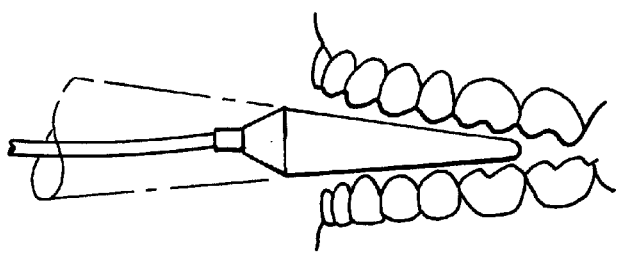

As shown in FIGS. 16, 17 and 18, many additional, different shapes to the apparatus 110 are illustrated. These provide varying shapes from which an oversertion sheath contour can be selected to perform specific, predetermined curing of a dental material in accordance with the specific application presented by the patient.

FIGS. 16(a) and (b) show dental curing apparatus for light-sensitive materials 110 having generally elongated shapes. In each of these shapes, the curing section 112 has a flattened conical or trapezoidal contour with a wider cross section at one end than at the other.

As shown in FIG. 17(a), this generally wedge shape better accommodates curing applications in the center of the teeth. A flattened, conical semi-rigid oversheath 114 is constructed and arranged, either by forming or molding, to receive and hold the curing apparatus 110 as in a bite chock type arrangement for curing occlusal dental materials.

A relatively straight, non-tapered shape to the housing 116 is shown in FIG. 17(b). Thus, a general use straight semi-rigid oversheath 114 is constructed and arranged, either by forming or molding, to receive and hold the curing apparatus 110 in proximity to a lingual surface of teeth in a quadrant. The apparatus 110 and sheath 114 may be held at least partially against lingual surfaces of teeth by the tongue. This relatively straight, non-tapered shape to the housing 116 is also more suitable to point curing restorative material on a tooth.

A curved, non-tapered shape to the housing 116, shown in FIG. 17(c), can further be fitted with a curved, semi-rigid oversheath 114 constructed and arranged to receive and hold the curing apparatus 110 in proximity to the gingival margins of teeth in a quadrant, or to accommodate occlusal curing of materials in teeth along anatomical curvatures in the mouth, e.g., along the Curve of Spee.

As further shown in FIG. 18, the housing 116 may have an elongated shape further having an elliptically rounded insertion end 144 with side contours 140, 142. The power receiving ends 146 may also be rounded, elliptical or flat. The housing insertion end 144 and/or the power receiving end 146 may both be flattened square surfaces. It is understood that, in any of the foregoing shapes and configurations, all edges would be rounded sufficiently so as to not project sharp edges during intra-oral use.

Thus, the varying shapes of housing and sheath combinations as described above function as both a sanitary shield for intraoral use and a matrix assembly using the outer surface of the sheath 116 to conform to the shape and/or contour of the restoration or cured material while held in place against the teeth or soft tissue. This facilitates longer intra-oral molding of light-sensitive acrylic-like materials for a final impression tray, thereby increasing the accuracy of the final impression tray.

Specific constructions of the light-providing features of the apparatus 110 are varied. For example, transparent and/or flexible organic light emitting devices (OLED), as from Universal Display Corporation, can be molded into the housing to work with or in place of an opto-electronic board. The housing shell can be shaped or molded or formed from OLED sheets and/or materials. Thus, an apparatus could be constructed to inherently emit curing light independent of any interior components, and may also be flexible.

Fresnel lens sheets or other thin film lenses can be inserted or molded into housings or may ne positioned over opto-electronic assemblies to help improve optical qualities. These may also work in conjunction with the variable shapes described for the contours of the apparatus 110, particularly as described in conjunction with FIG. 14.

As shown in FIG. 19, modifications to the apparatus surface 110 can result in better adaptation and function. A surface ridge 190, or channel-rounded projection, is molded into the curing section 112 to facilitate comfortable and optimal placement to conform to or to steady the position of the teeth during curing. As seen in cross-section, the ridge 190 is preferably provided with a base layer 192 positioned against at least one side of the curing section 112 and an outer ridge 194 positioned against the base layer 192, such that the base layer 192 is interposed between the curing section 112 and the outer ridge 194. As shown, the width of the base layer 192 is less than the width of the outer ridge 194. The width of the outer ridge 194 increases outwardly away from the base layer 192.

Although the preferred embodiments have been described as reusable, the apparatus can be either reusable or disposable, as specified by user instructions.

Disposable, custom formed or molded clear or translucent, semi-rigid oversheaths 116 having a specific shape to receive the curing apparatus 110 and accommodate any of several applications to optimally position the apparatus in the mouth have been disclosed. These can be constructed at various sizes to accommodate the mouth of an adult or the mouth of a child.

Thus, a dental curing apparatus for light-sensitive materials is disclosed. While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. For use in a human mouth containing teeth having a specific contour, a dental curing apparatus comprising, in combination:

a curing section and an oversertion sheath;

the curing section being reusable and having a light source for curing an adhesive contained within a housing constructed of a deformable, resilient plastic or elastomer;

the housing further having an insertion end oriented toward the human mouth into which the apparatus is placed and having at its opposite end a power receiving end for receiving an electrical current, the housing being sealed with respect to the light source for curing an adhesive such that the light source for curing an adhesive is maintained in non-contacting relation to the human mouth;

the oversertion sheath having a generally flattened, elongated shape and having a tapered sheath end oriented toward the human mouth into which the apparatus is placed and having at its opposite end a housing receiving aperture;

the oversertion sheath being constructed and arranged so as to receive the housing, the housing being constructed and arranged so as to be insertable into the oversertion sheath;

the oversertion sheath being selectable from a group of predetermined contours so as to be adaptable to perform specific, predetermined curing of a dental material in accordance with a specific application presented by a patient; and the curing apparatus having an overall length greater than approximately one inch and being conformable to the specific contour of the teeth within the human mouth with which it is to be used.

2. A dental curing apparatus according to claim 1 wherein the housing has a generally flattened, elongated shape.

3. A dental curing apparatus according to claim 1 wherein the housing is transparent.

4. A dental curing apparatus according to claim 1 wherein the housing is translucent.

5. A dental curing apparatus according to claim 1 wherein the oversertion sheath has a thickness of more than about 0.1 mm and less than about 2.0 mm.

6. A dental curing apparatus according to claim 1 wherein the oversheath has a flattened, conical contour constructed and arranged to secure the apparatus in a bite chock arrangement for curing occlusal dental materials.

7. A dental curing apparatus according to claim 1 wherein the oversheath has a straight, non-tapered contour constructed and arranged to secure the apparatus in proximity to a lingual surface of teeth in a quadrant.

8. A dental curing apparatus according to claim 1 wherein the oversheath has a curved, non-tapered contour constructed and arranged to secure the apparatus in proximity to the gingival margins of teeth in a quadrant.

9. An oversertion sheath for use with a dental curing apparatus constructed and arranged for use in a human mouth containing teeth having a specific contour, the oversertion sheath having a generally flattened, elongated shape and having a tapered sheath end oriented toward the human mouth into which the apparatus is placed and having at its opposite end a housing receiving aperture;

the oversertion sheath being constructed and arranged so as to receive a housing constructed and arranged so as to be insertable into the oversertion sheath;

the oversheath having a curved, non-tapered contour constructed and arranged to accommodate occlusal curing of materials in teeth along anatomical curvatures in the mouth so as to be adaptable to perform specific, predetermined curing of a dental material in accordance with a specific application presented by a patient.

10. An oversertion sheath according to claim 9 wherein the oversheath has a flattened, conical contour constructed and arranged to secure the apparatus in a bite chock arrangement for curing occlusal dental materials.

11. An oversertion sheath according to claim 9 wherein the oversheath has a straight, non-tapered contour constructed and arranged to secure the apparatus in proximity to a lingual surface of teeth in a quadrant.

12. For use in a human mouth containing teeth having a specific contour, a dental curing apparatus comprising, in combination:

a curing section and an oversertion sheath;

the curing section being reusable and having a light source for curing an adhesive contained within a housing;

the housing further having an insertion end oriented toward the human mouth into which the apparatus is placed and having at its opposite end a power receiving end for receiving an electrical current, the housing being sealed with respect to the light source for curing an adhesive such that the light source for curing an adhesive is maintained in non-contacting relation to the human mouth;

the oversertion sheath having a generally flattened, elongated shape and having a tapered sheath end oriented toward the human mouth into which the apparatus is placed and having at its opposite end a housing receiving aperture;

the oversertion sheath being constructed and arranged so as to receive the housing, the housing being constructed and arranged so as to be insertable into the oversertion sheath;

the oversheath having a curved, non-tapered contour constructed and arranged to accommodate occlusal curing of materials in teeth along anatomical curvatures in the mouth so as to be adaptable to perform specific, predetermined curing of a dental material in accordance with a specific application presented by a patient; and the curing apparatus having an overall length greater than approximately one inch and being conformable to the specific contour of the teeth within the human mouth with which it is to be used.

13. A dental curing apparatus according to claim 12 wherein the oversheath has a flattened, conical contour constructed and arranged to secure the apparatus in a bite chock arrangement for curing occlusal dental materials.

14. A dental curing apparatus according to claim 12 wherein the oversheath has a straight, non-tapered contour constructed and arranged to secure the apparatus in proximity to a lingual surface of teeth in a quadrant.

15. A dental curing apparatus according to claim 12 wherein the housing has a generally flattened, elongated shape.

* * * * *